United States Patent [19]

Kornfeind

[11] Patent Number: 4,995,509

[45] Date of Patent: Feb. 26, 1991

[54] DISPOSABLE TOOTHBRUSH SANITIZING AND STORAGE DEVICE

[76] Inventor: Joseph Kornfeind, 124 Hillcrest Dr., Coplay, Pa. 18037

[21] Appl. No.: 516,543

[22] Filed: Apr. 30, 1990

[51] Int. Cl.[5] .......... B65D 25/20

[52] U.S. Cl. .......... 206/209.1; 206/205; 206/209; 206/362; 206/362.1; 206/362.3; 211/65; 211/75

[58] Field of Search .......... 206/205, 209, 209.1, 206/212, 361, 362, 362.1, 363.2, 362.3, 15.2, 15.3; 15/184, 248 R, 256.5; 248/146, 147; 211/65, 75, 76

[56] References Cited

U.S. PATENT DOCUMENTS

| | | | |
|---|---|---|---|
| 1,079,618 | 11/1913 | Trayne | 206/15.3 |
| 1,228,261 | 5/1917 | Taylor | 206/362.1 |
| 1,278,789 | 9/1918 | Thompson | 206/209.1 |
| 1,987,472 | 1/1935 | Feldon | 206/209.1 |
| 2,816,667 | 12/1957 | Tanay | 211/76 |
| 3,574,879 | 4/1971 | Werding | 206/362.2 |
| 3,759,375 | 9/1973 | Nappi | 206/210 |
| 3,867,096 | 2/1975 | Doucette | 206/205 |
| 3,881,868 | 5/1975 | Duke | 206/209.1 |
| 4,585,119 | 4/1986 | Boyington | 206/209.1 |
| 4,776,456 | 10/1988 | Lewis | 206/15.3 |
| 4,915,219 | 4/1990 | Ottimo | 206/209.1 |

*Primary Examiner*—David T. Fidei
*Attorney, Agent, or Firm*—John J. Selko

[57] ABSTRACT

A disposable device for simultaneously storing and cleaning a toothbrush includes a support base and a removable storage receptacle. Within the storage receptacle is located a liquid disinfectant and bristle arms to contact and clean the body portion and bristles of a toothbrush during the insertion and removal of the toothbrush. A strippable plastic seal closes the receptacle until the time of use.

5 Claims, 3 Drawing Sheets

1
3
7
5
9
15
15
15
13
31
39
11
33
23
29

43
17
31
41
41
43
31
43
27
25
5
39
21
19
33
35
35
23
23
29
37

4
55
15
45
17
9
31
39
23
33
35
35
47
49
21
19
4

55
45
15
15
9
31
39
39
31
39
53
35
35
33
33
55
51
21
47
49

45
27
17
65
25
11
9
31
61
63
33
3
23
5
67

77
75
73
81

23
79
71

DISPOSABLE TOOTHBRUSH SANITIZING AND STORAGE DEVICE

BACKGROUND OF THE INVENTION

1. Field of the Invention

This invention relates to devices for storing and sanitizing toothbrushes. More particularly, it relates to devices that are disposable, and thereby suitable for supply to the public for short-term use by organizations such as hospitals and hotels. Also, it relates to disposable devices that can be replaced periodically, as the effectiveness as the sanitizing disinfectant agent becomes diminished through prolonged use.

2. Description of the Prior Art

Typical of sanitizing devices are the disclosures in the following U.S. Pat. Nos.: 4,585,119; 1,079,618; 1,228,261; 3,759,375; 1,746,815; 3,904,362, and 4,214,657. Such devices show various combinations of holders and disinfectant.

OBJECTS

A principal object of this invention is the provision of a new and improved device for simultaneously storing and cleaning a toothbrush, including cleaning the bristles and body portion of the toothbrush to which the bristles are affixed. A further object includes the provision of a disposable device for said storage and cleaning functions, said device having a readily replaceable storage member easily removed from a substantially permanent support base.

Other objects and further scope of applicability of the present invention will become apparent from the detailed description given hereinafter; it should be understood, however, that the detailed description, while indicating preferred embodiments of the invention, is given by way of illustration only, since various changes and modifications within the spirit and scope of the invention will become apparent to those skilled in the art from this detailed description.

SUMMARY OF THE INVENTION

The objects are accomplished by the provision of a device having a support means carrying one or more removable toothbrush storage receptacles. Each receptacle has sealed within it, by a strippable plastic seal, suitable liquid disinfectant and bristle means for contacting a toothbrush body and bristles thereon during insertion and removal of the toothbrush.

DETAILED DESCRIPTION OF THE PREFERRED EMBODIMENT

Figure 1:
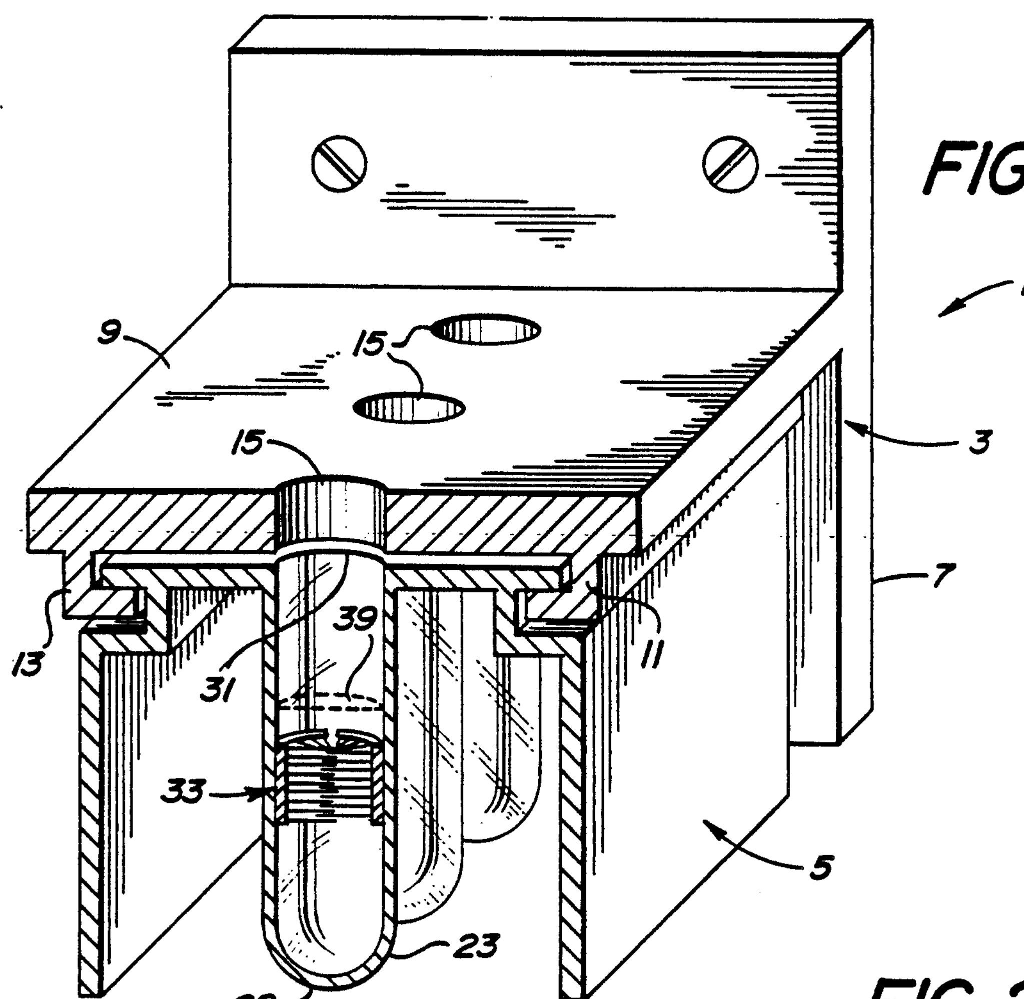
FIG. 1 is a perspective view of the invention, partially in cross section, with parts removed, for mounting on a vertical surface.

Referring to FIG. 1 the device 1 is shown to comprise a first support means 3 carrying a toothbrush storage means 5 removably mounted on support means 3. The first support means 3 is suited for affixing the device 1 to a vertical surface, such as a bathroom wall, not shown. Support means 3 includes a vertically extending back plate 7, and a shelf 9 extending horizontally outwardly from back plate 7. Extending below-shelf 9, at about the corners thereof, is a pair of oppositely-spaced, parallel, L-shaped, sliding rails 11 and 13 extending outwardly from back plate 7, from which toothbrush storage means 5 is slidably suspended for removal and insertion. A plurality of apertures 15 extend vertically downward through shelf for receiving a toothbrush as described hereinafter.

Figure 2:
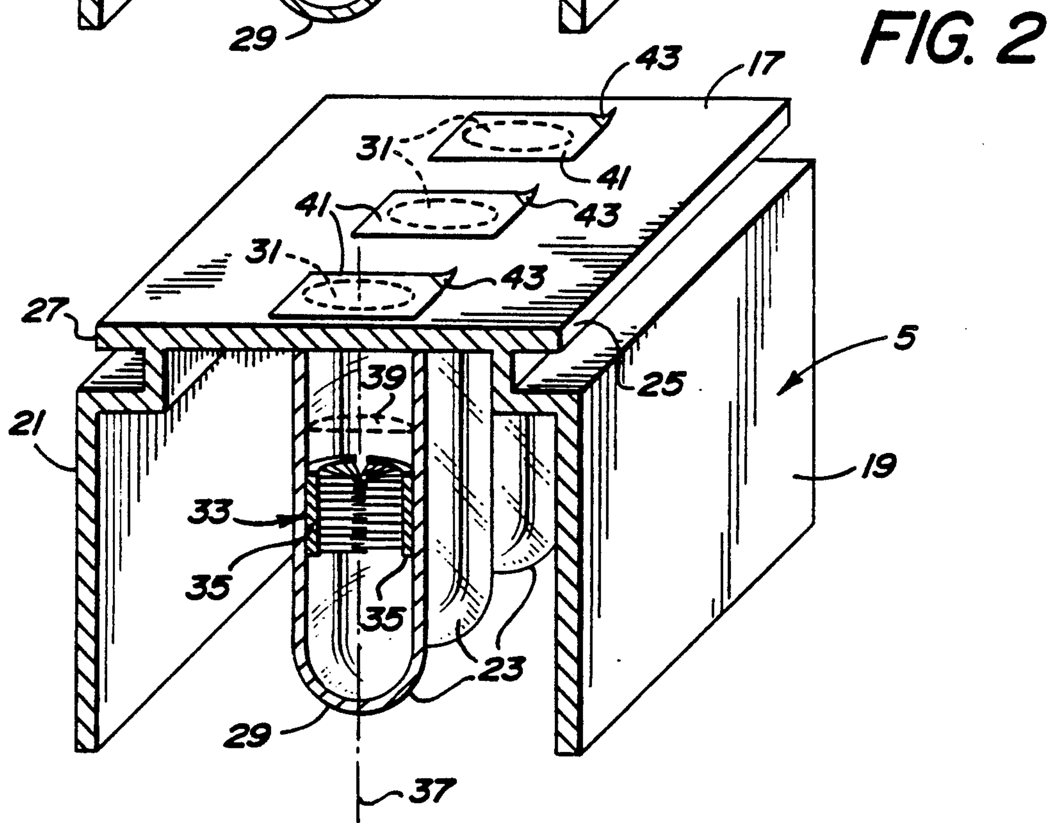
FIG. 2 is a perspective view of the disposable toothbrush storage means, partially in cross section with parts removed, showing three receptacles sealed with a strippable cover means.

Referring to FIG. 2 the disposable toothbrush storage means 5 is shown to comprise a top surface 17 extending horizontally between a pair of spaced apart parallel, vertically extending side walls 19 and 21. Not shown is a vertically extending front wall extending between side walls 19 and 21. A rear wall (not shown) is optional. Extending downwardly from top surface 17 is a plurality of toothbrush receptacles 23. Three are shown, but fewer or more can be used. The spacing arrangement among receptacles 23 is optional.

A pair of oppositely-spaced, U-shaped, parallel sliding rails 25 and 27 extended horizontally outwardly from back plate 7 on the upper corners of toothbrush storage means 5, and engage and slide along rails 11 and 13, to removably suspend toothbrush storage means 5 from first support means 3.

Each receptacle 23 comprises a closed bottom end 29, an open top end 31, and bristle means 33 within each receptacle 23. Bristle means 33 is affixed to the interior wall of receptacle 23 about half-way between bottom end 29 and top end 31. Any suitable means, such as adhesive, will do to affix bristle means 33 to receptacle 23. Bristle means 33 has oppositely spaced bristle arms 35 extending inwardly to meet at about the vertical center line 37 of receptacle 23. Bristles arms 35 are flexibly deformable, to permit a toothbrush (not shown) to pass vertically therethrough. (See FIG. 3 and 4).

Inside each receptacle 23 is a suitable disinfectant liquid, 39. The level of disinfectant 39 is preferably entirely above bristle means 33, but it could be somewhat lower, so as to substantially cover bristle means 33. Across top end 31 of each receptacle 23 is affixed a strippable plastic sealing strip 41. Strip 41 is adhesively affixed to top end 31 to retain liquid 39 in receptacle 23 until the time of use. A corner 43 on each strip 41 is not affixed, so as to provide a member for grasping, to remove strip 41. Strip 41 being a flexible plastic, can be selected of a suitable thickness to permit forceful puncture by a suitable instrument, instead of removal by stripping. The entire toothbrush storage means 5 can be made of transparent material, or, alternatively, only receptacles 23 can be transparent, to permit viewing of the condition of the contents of receptacles 23.

Figure 3:
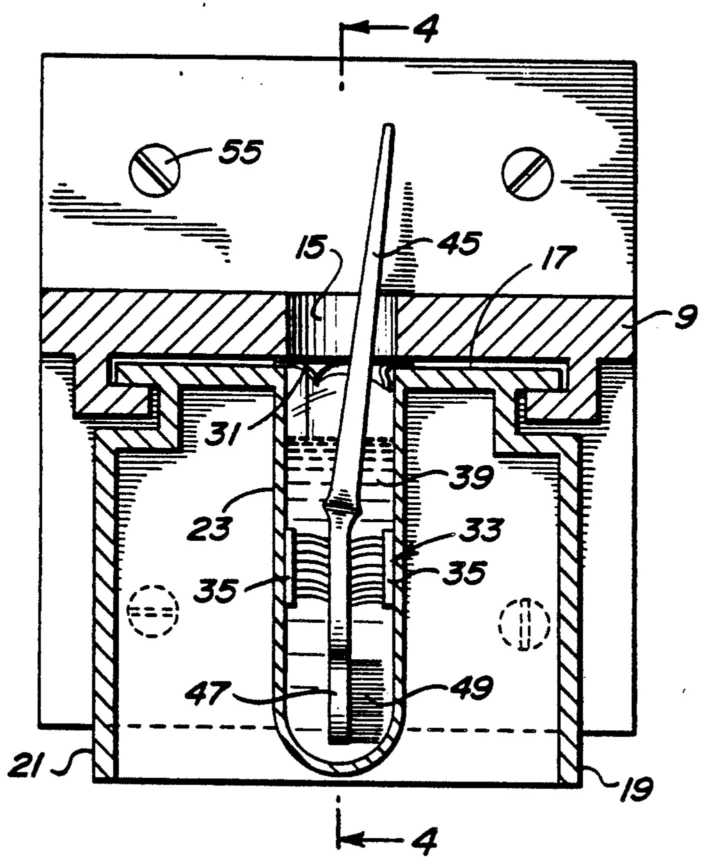
FIG. 3 is a front elevational view, in section, with parts removed, showing a toothbrush in place.
Figure 4:
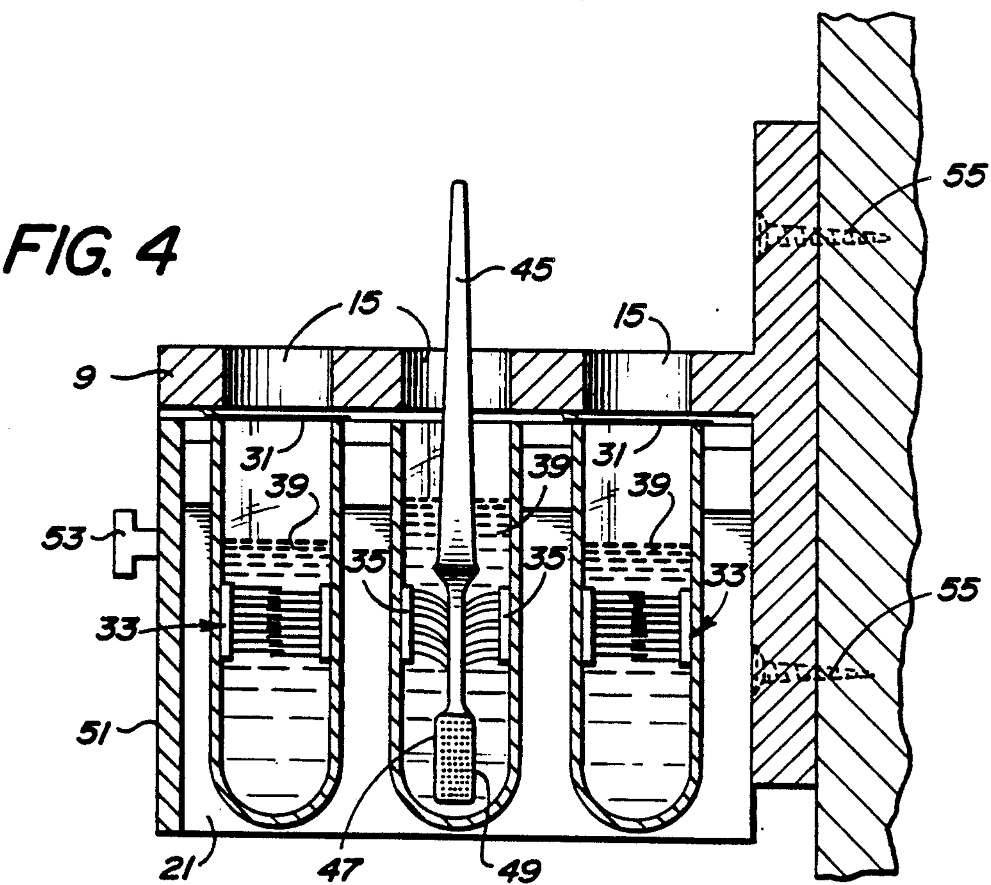
FIG. 4 is a view along 4—4 of FIG. 3.

Now referring to FIGS. 3 and 4, a toothbrush 45 having an end body portion 47 and bristles 49 affixed to end body portion 47 is shown inserted into receptacle 23. Bristle means 33, having oppositely spaced bristle arms 35 extending into the centerline 37 of receptacle 23, continuously contacts the end body portion 47 and bristles 49 affixed to end body portion 47 during the insertion and withdrawal of toothbrush 45 into receptacle 23. This contact between bristle means 33 and toothbrush 45 acts to clean the portions contacted, and the disinfectant 39 sanitizes toothbrush 45 between uses. The apertures 15 in shelf 9, are spaced apart in a configuration to position an aperture 15 vertically above a top end 31 of a tubular receptacle 23, with toothbrush storage means 5 fully inserted into first support means 3. As shown in FIG. 4, front wall 51 extends between side walls 19 and 21. Handle 53 on front wall 51 permits slidable insertion, and removal of toothbrush storage means 5 for disposal, after all receptacles 23 have been used. FIGS. 3 and 4 show the device 1 for mounting with screws 55 to a vertical surface.

Figure 5:
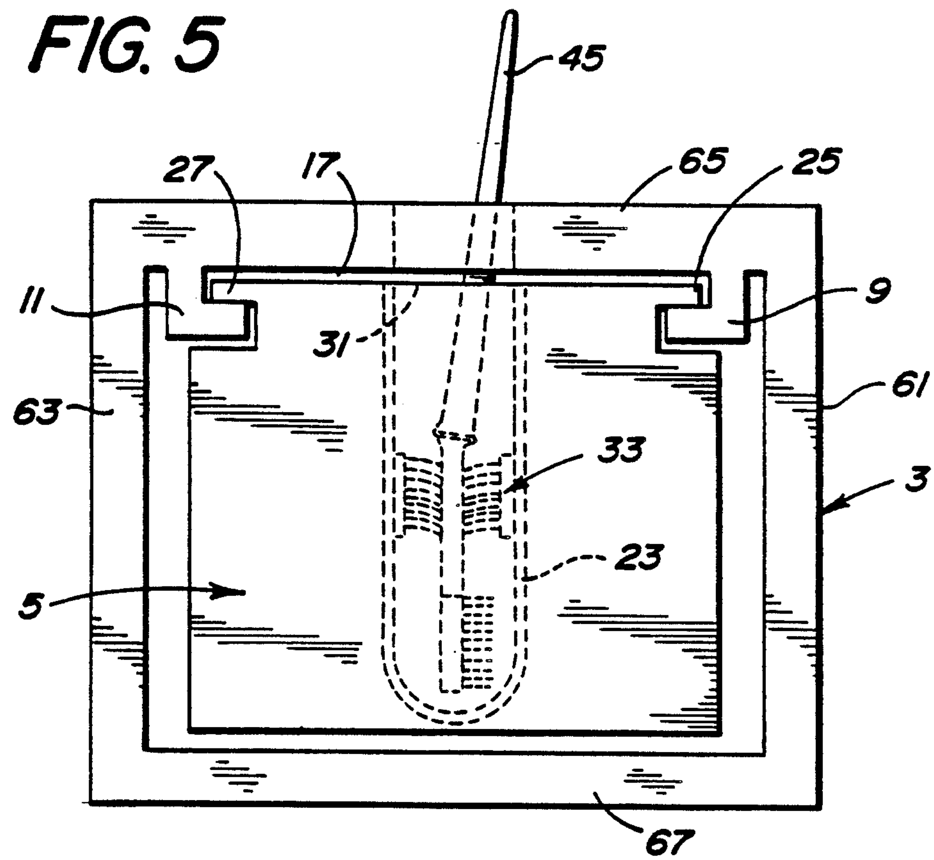
FIG. 5 is a front elevational view of an alternate embodiment of the invention.

Alternatively, the first support means 3 could be designed to be free-standing on a horizontal surface, as shown in FIG. 5. First support means 3 would include a pair of spaced apart vertically extending parallel side walls 61, 63 connected by top wall 65 and a bottom wall 67 parallel to top wall 65. L-shaped slide 9 rails and 11 and U-shaped slide rails 25, 27 interact as described hereinabove to permit toothbrush storage means 5 to be slidably inserted in first support means 3 for eventual removal.

For both embodiments described hereinabove, the proximity of top surface 17 of toothbrush storage means 5 and the bottom surface of wall 65 (of shelf 9) generally acts as a shield, or cover, to the opening 31 of each receptacle, to enhance sanitary storage.

Figure 6:
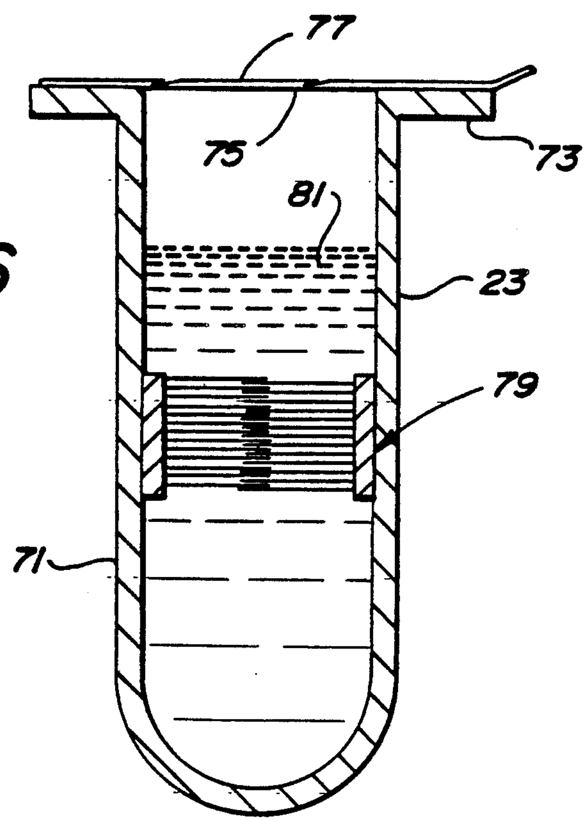
FIG. 6 is an elevational view of an alternate embodiment of the invention, involving a removable toothbrush receptacle.

In another embodiment, as shown in FIG. 6, each receptacle 23 can be individually removable from the device. Receptacle 23 consists of a tubular storage body 71 and a flanged end 73 surrounding top opening 75. Sealing strip 77 extends across opening 75, and bristle means 79 and disinfectant 81 are located within receptacle 23, as described hereinabove. Receptacle 23 can be dropped into aperture 15, to rest flange 73 on the top surface of shelf 9. Or, alternatively, receptacle 23 can be removably inserted into an aperture in top surface 17 of toothbrush storage means 5.

I claim:

1. A disposable device for simultaneously storing and cleaning a toothbrush, said toothbrush having an end body portion and bristles affixed to said end body portion comprising:

a. a first support means for supporting the device on a surface;

b. a disposable toothbrush storage means removably mounted on the first support means, for receiving one or more toothbrushes;

c. said toothbrush storage means comprising one or more downwardly extending tubular toothbrush receptacles, each receptacle further comprising;

i. a closed bottom end and an open top end;

ii. bristle means within each receptacle, having oppositely spaced, flexibly deformable bristle arms extending inwardly to meet at about a vertical centerline of said receptacle, for continuously contacting the bristles and end body portion of a toothbrush during insertion and withdrawal of a toothbrush into said receptacle;

iii. liquid disinfectant within each receptacle to a level to substantially cover said bristle means; and iv. a strippable cover means secured to the open end of each receptacle, for retaining the disinfectant therein, until a toothbrush is inserted into said receptacle.

2. A disposable device for simultaneously storing and cleaning a toothbrush, said toothbrush having an end body portion and bristles affixed to said end body portion comprising:

a. a first support means for supporting the device on a surface;

b. a disposable toothbrush storage mens removably mounted on the first support means, for receiving one or more toothbrushes;

c. said toothbrush storage means comprising one or more downwardly extending tubular toothbrush receptacles, each receptacle further comprising;

i. a closed bottom end and an open top end;

ii. bristle means within each receptacle for contacting the bristles and end body portion of a toothbrush during insertion and withdrawal of a toothbrush into said receptacle;

iii. liquid disinfectant within each receptacle to level to a substantially cover said bristle means; and iv. a strippable cover means secured to the open end of each receptacle, for retaining the disinfectant therein, until a toothbrush is inserted into said receptacle; and d. said support means comprising:

i. a vertically extending back plate;

ii. means for affixing said back plate to a vertical surface;

iii. a shelf extending horizontally outwardly from said back plate;

iv. means for removably suspending a toothbrush storage means vertically below said shelf; and v. one or more apertures in said shelf, spaced apart in configuration to position an aperture vertically above a top end of a tubular receptacle when said toothbrush storage means is slidably mounted on said shelf.

3. The invention of claim 2 in which said disposable toothbrush storage means includes a top surface extending horizontally between a pair of spaced apart, parallel, vertically extending sidewalls.

4. The invention of claim 3 in which the means for removably suspending said toothbrush storage means vertically below said shelf includes:

a. a pair of oppositely-spaced, parallel L-shaped, sliding rails extending horizontally outwardly below said shelf;

b. a pair of oppositely-spaced, parallel, U-shaped, sliding rails extending horizontally outwardly on the upper corners of said toothbrush storage means, for engaging and sliding on said L-shaped sliding rails.

5. The invention of claim 1 in which said strippable cover means is a flexible plastic of sufficient thickness to permit forceful puncture by an object.

* * * * *